United States Patent [19]

Hutter, III

[11] 3,955,570
[45] May 11, 1976

[54] SURGICAL EXHAUST MASK
[75] Inventor: Charles G. Hutter, III, Hollywood, Calif.
[73] Assignee: Physical Systems, Inc., Hollywood, Calif.
[22] Filed: May 17, 1974
[21] Appl. No.: 470,985

Related U.S. Application Data
[63] Continuation-in-part of Ser. No. 252,069, May 18, 1972, abandoned.

[52] U.S. Cl............................ 128/142.7; 128/142.3; 2/DIG. 7; 128/139
[51] Int. Cl.² ........................................... A62B 7/02
[58] Field of Search............ 128/142.7, 139, 140 R, 128/141 R, 142, 142.3–142.5, 146.2, 146.6, 146.7; 2/173, 171.3, 14 B, 14 K, 14 N, DIG. 1, DIG. 7, 5, 6, 9

[56] References Cited
UNITED STATES PATENTS
| 1,947,137 | 2/1934 | Fraser | 2/14 N |
| 3,529,594 | 9/1970 | Charnley | 128/139 |
| 3,668,705 | 6/1972 | Garbisch | 2/173 |

Primary Examiner—Robert W. Michell
Assistant Examiner—Henry J. Recla
Attorney, Agent, or Firm—Fulwider Patton Rieber Lee and Utecht

[57] ABSTRACT

Mask includes support member with head band arranged horizontally to fit head of wearer. Conduit sections are secured to each side of support member, and flexible ventilation conduit is connected to exhaust means. Transparent face plate is held to support member in spaced relation to wearer's head. Aperture means in conduit allow ingress of air, and exhaust means connected to conduit sections exhaust air from ventilation conduit and interior of mask. In one form, means in upper portion of face plate admit airflow and direct it down over inner surface of face plate to prevent fogging. Hood of air-impermeable material fits over head and shoulders. Gown of similar material over body and lower part of hood and tied at neck completes assembly. Any leakage is that of sterile air from exterior to interior of mask because of continuously operating exhaust system.

5 Claims, 16 Drawing Figures

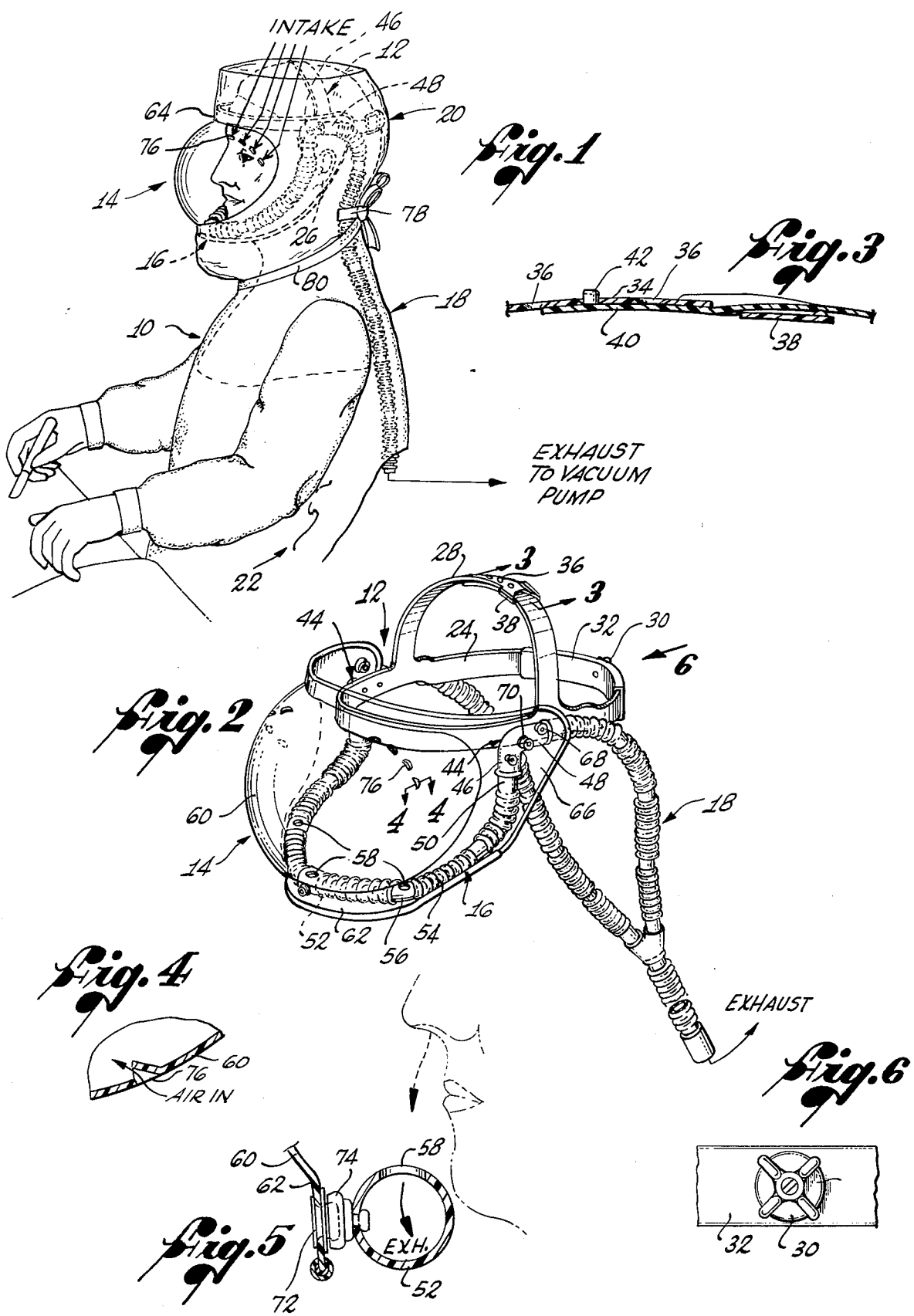

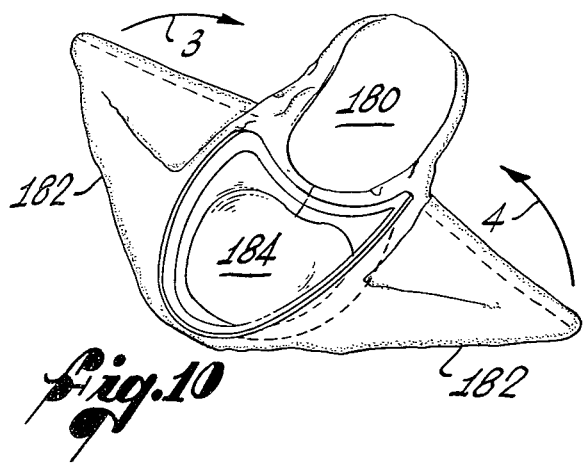
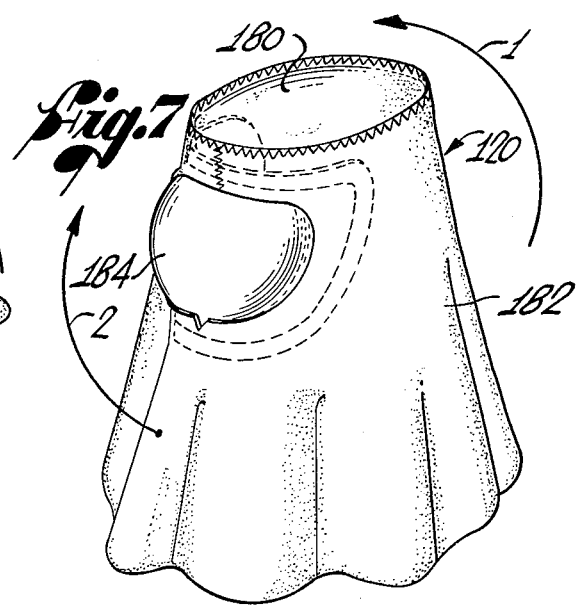
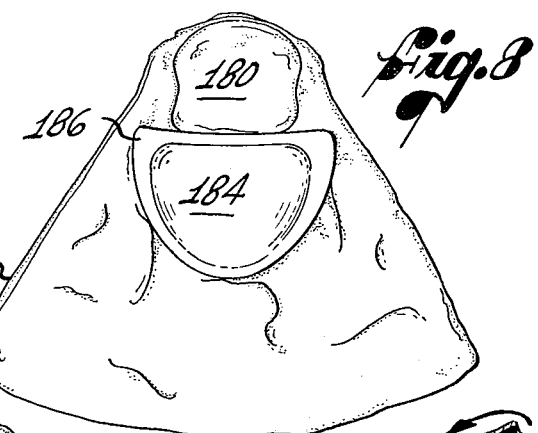
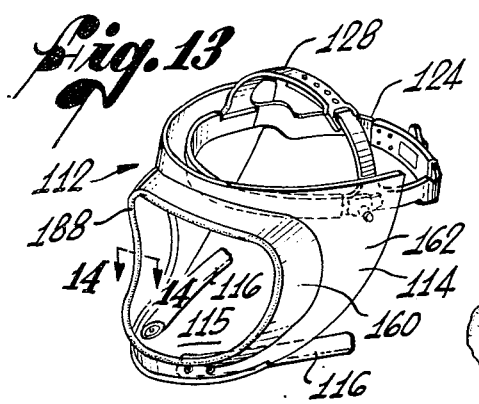
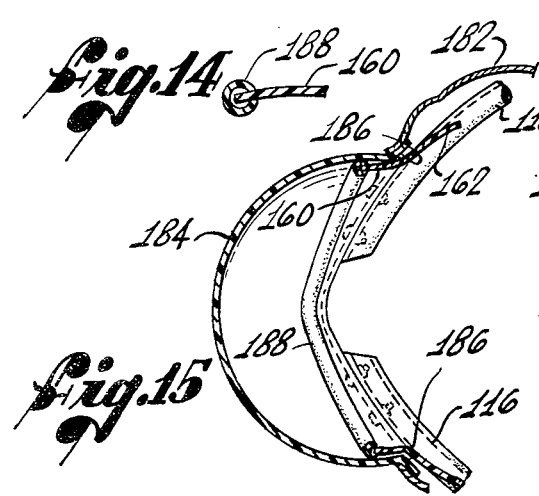
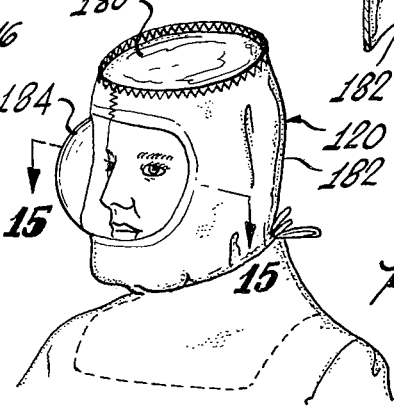

SURGICAL EXHAUST MASK

BACKGROUND OF THE INVENTION

This is a continuation-in-part of my earlier patent application, Ser. No. 252,069, filed May 18, 1972 and now abandoned, entitled "SURGICAL EXHAUST MASK".

This invention lies in the field of masking systems to prevent contamination of the air in any location where it is desired to maintain "clean air" conditions to avoid corrosion or deposit of dust or moisture or other contaminants. It is more particularly directed to a masking system for use in the performance of surgical operations.

One of the problems which has plagued the medical profession for many years is post-operative infection resulting from contamination of open wounds during surgery. There are many possible causes of such contamination, such as contaminated instruments and hands, perspiration and respiratory droplets and shedding of hair and skin of the surgeon, and the bacteria on the skin of the patient. Most of these problems have been greatly reduced by presently used techniques, including preoperative skin cleaning, the surgical scrub, rubber gloves, masks, sterile drapes, clothing, and instruments, and thorough filtration of the air in the operating theatre. However, some contamination and infection still exists, and efforts are continually being made to improve the situation.

One of the sources of contamination which is very difficult to control is the surgeon himself. Of necessity, he must be immediately adjacent the patent and in fact, leaning directly over the locus of the surgery. His gown and hood are not totally impervious to passage of perspiration moisture and epithelial scales and bacteria from the body. The conventional surgical mask is merely a coarse filter which removes bacterialaden droplets of moisture from the exhaled breath. This mask soon becomes saturated with water preventing easy passage of air through the material. The exhaled air is thus directed out around the edges of the mask. This re-direction of moist air upward around the nose and cheeks causes fogging of spectacles and general discomfort to the surgeon.

Considerable improvement has resulted from equipping operating rooms with means for producing a continuous laminar flow of sterile air through the room from one side wall to the opposite wall or from ceiling to floor. The flow carries the majority of contaminants out of the room before they can come into contact with the patient, but every movement of any member of the operating team disturbs the laminar flow and reduces its effectiveness. In addition, the surgical team working in close proximity to the surgical site provides a concentrated source of bacteria which can be carried by the flowing air into the wound.

An answer to this problem has been the provision of exhaust type masking systems in which the members of the operative personnel are substantially completely covered with a hood and gown of practically impermeable material and closed transparent mask located in an opening in the front of the hood. A conduit system is connected to a suction manifold and has a suction opening adjacent the face of the wearer to carry away exhalations, perspiration, etc. There is negative pressure throughout the interior of the gown so that any leakage is inward. The masks which have been used to date have been rather clumsy and physically uncomfortable and have acted like blinders to seriously reduce the range of vision of the wearer, both vertically and laterally. Experiments have been made recently with suits similar to those worn by the astronauts in space exploration. While visibility is improved, the apparatus is heavy and cumbersome and requires a great deal of time to assemble in place.

SUMMARY OF THE INVENTION

The masking system of the present invention overcomes the difficulties mentioned above and provides a relatively light and simple apparatus which is quick and easy to assemble in place, comfortable to wear, and highly effective, while providing maximum visibility in all directions and good aural communication.

Broadly, two forms of the exhaust mask are shown. The first form makes use of a support member to which a face plate is removably attached, and a disposable hood is placed over the support and face plate, an aperture in the hood aligning with the face plate to insure wide-angle vision for the wearer. The second form makes use of a support member carrying an apertured plate in front of the face of the wearer, and a disposable hood carrying a disposable face plate is placed over the support with the disposable face plate making a sealing fit with the apertured plate.

The first form of mask includes a support member shaped and sized to fit the head of the wearer, with a head band arranged horizontally to surround the wearer's head. An angular rigid conduit section is secured by its inner side to each side of the head band in such position that its first end will extend downwardly forward of the wearer's ear and its second end will extend aft above the wearer's ear. A U-shaped ventilation conduit is arranged in generally upright position with its upper ends connected to the conduit sections and its lower central bight portion in a position adjacent the wearer's chin.

A transparent face plate is provided to extend across the face of the wearer and preferably includes a main body having the general configuration of a portion of a sphere, and a margin extending at an angle to the surface of the main body to serve as a relatively flat flange for sealing engagement with the marginal portion of the opening in a hood to be worn therewith. The upper portions of the margin extend aft a substantial distance and are connected to the outer sides of the rigid conduit sections, while the bight portion of the ventilation conduit is connected to the inside of the lower central margin to hold the parts in assembled relation.

One or more apertures are formed in the upper side of the bight portion of the ventilation conduit, and suction conduit means are connected to the second ends of the rigid conduit sections and are adapted to be connected to a suction manifold to draw air in through the apertures and exhaust it from the ventilation conduit. In order to prevent fogging from the breath of the wearer, openings are formed in the upper part of the main body and oriented to direct the inflow of air inward and downward to flow across the inner surface of the main body, thus preventing deposition of any moisture.

The generally spherical surface of the main body extends aft of the location of the wearer's eyes, so that he has maximum lateral visibility. The soft ventilation conduit spaces the rigid face plate away from the wearer's head to insure comfort and also to provide an open path for communication. A hood is provided which covers the head and shoulders and has an opening matching the periphery of the main body, and a gown covers most of the remainder of the wearer's body and overlaps the lower portion of the hood. A draw string at the top is loosely tensioned about the wearer's neck to provide a low-leak assembly. The suction system draws air through the gown to provide a cooling airflow for the wearer's body and remove any contaminants, and the negative internal pressure insures that any air leakage will be from exterior to interior.

The second form of mask makes use of a support member, generally similar to that of the first form, with an apertured plate attached to the support member to cover the face of the wearer. A disposable hood, usually of a special paper, carries a face plate whose shape and extent approximate that of the "main body" of the first form. Resilient sealing means establish a seal between the apertured plate and the face plate, and an air exhaust system substantially similar to that of the first form exhausts the air from the mask.

The second form is, of course, intended to be kept clean at all times, but only the hood and the face plate must be sterilized, thus considerably simplifying sterilization procedures. Since the face plate of the first form is removably attached to the support member, the face plate must be sterilized before each use, in addition to sterilizing the hood.

BRIEF DESCRIPTION OF THE DRAWINGS

Various other advantages and features of novelty will become apparent as the description proceeds in conjunction with the accompanying drawings, in which:

FIG. 1 is a perspective view of a surgeon wearing the complete assembly of the invention including mask, hood, and gown;

FIG. 2 is a perspective view of the principal components of the mask in assembled relation;

FIG. 3 is a sectional view taken on line 3—3 of FIG. 2;

FIG. 4 is a sectional view taken on line 4—4 of FIG. 2;

FIG. 5 is a fragmentary sectional view illustrating the relation of the exhaust system to the wearer;

FIG. 6 is an elevational view of an adjustment device looking in the direction of arrow 6 in FIG. 2;

FIG. 7 is a perspective external view of a hood with attached face plate of the second form of invention, the view being taken from slightly above the front left side;

FIG. 8 is an elevational view of the interior of the hood with the back portion folded up and over the crown;

FIG. 9 is a cross-sectional view taken through the vertical centerline of FIG. 8 showing the relative position of the various members after the front of the hood has been folded up, over the face plate and under the back of the hood;

FIG. 10 is a view similar to FIG. 8, showing the position of the various elements when the hood is in the condition indicated in FIG. 9;

FIG. 11 shows the next step in the folding of the hood, with the left section folded onto the face plate and the right section about to be folded;

FIG. 12 shows the completely folded hood;

FIG. 13 is a perspective view of the support member used in conjunction with the hood with attached face plate shown in FIG. 7;

FIG. 14 is a cross-sectional view taken on the line 14—14 of FIG. 13 and showing the sealing member;

FIG. 15 is a fragmentary horizontal cross-sectional view of the hood and support member, taken on the line 15—15 of FIG. 16; and FIG. 16 is a front left perspective view of the mask as it appears in use.

DESCRIPTION OF FIRST EMBODIMENT

The complete assembly of the first form of mask in operative position is illustrated in FIG. 1, in which an individual 10, such as a surgeon, wears a support member 12, to which is attached a face plate 14, a ventilation conduit 16, and exhaust conduit means 18. A hood 20 fits over the head and shoulders, and a sleeved gown 22 overlaps the lower end of the hood and is gathered at the neck.

Considering FIG. 2, the support member 12 includes a head band 24 to surround the wearer's head in a generally horizontal attitude above his ears 26, and a cross band 28 to extend laterally across his head and hold the head band at the proper elevation. The head band is tightened to form a snug fit by means of the ratchet knob 30 shown in FIG. 6. Two free ends of the head band are provided with suitable ratchet formations and slide in overlapping relation within housing 32. Knob 30 has an appropriate pinion formation within the housing to engage the bands and retract or extend them.

The cross band is also provided with adjusting means as shown in FIGS. 2 and 3. One free end portion 34 is formed with a plurality of apertures 36 and an end loop 38. The other free end portion 40 is slidably mounted in loop 38 and is formed with a boss 42 which may be snapped into any one of the apertures 36 to produce the desired band length.

A rigid conduit section 44, preferably of plastic material, has an angular form similar to a typical plumbing pipe elbow, and one section is attached at its inner side, preferably by rivets, to each side of the head band so that a first end 46 extends downward and a second end 48 extends aft. These conduit sections are located at such positions along the head band that their first ends extend forward of the wearer's ears and the second ends extend above his ears, as indicated in FIG. 1.

Ventilation conduit 16 is U-shaped with its two upper ends 50 flow-connected to ends 46 of the rigid conduit sections and its lower central bight portion 52 located to be in a position close to the wearer's chin. Conduit 16 is quite flexible with thin, bellows-type walls 54 and spaced cylindrical sections 56. One or more of these sections 56 is formed with apertures 58 in the upper sides for ingress of air during operation.

Face plate 14 is carried by support member 12 through the intermediary of ventilation conduit 16 and rigid conduit sections 44. It comprises a transparent main body 60 which may be a cylindrical section, but preferably has the general configuration of a portion of a sphere. Its entire perimeter is surrounded by a margin 62 extending at a substantial angle to its surface to form a generally flat flange for sealing engagement by the marginal portion 64 of the opening in hood 20. The upper lateral portions 66 of the margin extend a substantial distance aft of the main body and are provided with a plurality of vertically and diagonally spaced fastener members 68 selectively engageable with a mating fastener member 70 secured to each of the rigid conduit sections 44. The lower central portion of the margin is provided with a single fastener member 72 which is engaged with a mating fastener member 74 fixed to the front wall of the central bight portion 52 as shown in FIG. 5.

When the mask is donned, the wearer or an assistant snaps the appropriate fastener member 68 to its mating fastener member 70 to bring bight portion 52 to the position shown in FIG. 5. When properly adjusted, the bight portion is adjacent the chin rather than below it or close to the mouth, and will ordinarily contact the chin lightly to maintain the position of the face plate. By the use of snap fasteners, the face plate may be readily and quickly disconnected from the ventilation conduit and rigid conduit sections for cleaning and polishing.

Aperture means 76 are formed in the upper portion of main body 60 for ingress of air. These may be elongate slots, but preferably are a plurality of individual apertures, as shown. The flow axis of each aperture is angled inward and downward, as illustrated in FIG. 4, to direct the inflow air in a path close to the inner surface of the main body and prevent the deposition of any moisture which would fog the surface.

Regardless of the configuration of the main body 60, it is brought around laterally and rearward sufficiently to extend aft of the wearer's eyes, so that he will have maximum lateral visibility. In the preferred substantially spherical form, the lateral extent is approximately 180° and the vertical extent is approximately 90°, giving maximum visibility in all directions.

Since the rigid conduit sections are attached by their inner sides to the head band and the face plate margins are attached to the outer sides of the rigid conduit sections, and the ventilation conduit is entirely within the face plate, only the relatively soft ventilation conduit will touch the sides of the face and chin, and the rigid face plate is entirely out of contact with the head, thus greatly reducing the discomfort of wearing the device. Also, it will be noted that the ventilation conduit is forward of the ears, leaving a sound path blocked only by the thickness of the hood material. Consequently, aural communication is facilitated and no electronic devices are necessary.

While the margin 62 may be a separate unit made of metal or other opaque material because it would not be in the viewing range, it is preferred to make the entire face plate as a single molding of transparent plastic.

As previously mentioned, hood 20 fits over the head, and drapes down over the shoulders, as illustrated in FIG. 1, with its opening fitting over the main body 60 of the hood and with the marginal portion 64 of the hood in sealing contact with the margin 62 of the main body. The main body 60 then projects through the opening of the hood 20 to provide an unobstructed, wide angle of view, and the hood is held snugly in this position by the back tie 78. Gown 22 covers most of the balance of the body and overlaps the lower portion of the hood at its upper end, which is provided with a draw string 80, tensioned about the neck to produce a low-leakage connection.

When the exhaust conduit means 18 is connected to a suction manifold, preferably through a "Y" connection and additional flexible tubing, air is constantly withdrawn through it. Consequently, air is drawn in through apertures 58 and exhausted through the ventilation conduit. The rate of exhaust flow is sufficient to withdraw the exhalations of the wearer, draw fresh air through apertures 76, and create a negative pressure in the hood and gown. The negative pressure holds marginal portion 64 in sealing contact with margin 62 and insures that any leakage at the draw string joint or through the hood or gown material will be from exterior to interior. The continual exhaust further produces a cooling flow of air up within the gown to greatly increase the comfort of the wearer.

DESCRIPTION OF SECOND EMBODIMENT

The second form of device is basically similar to the first form just described, but incorporates the face plate in the hood so that the two are sterilized in one operation. This change means that sterilization is much simpler, and it is possible for the surgeon or attendant to place the hood on the surgeon with less work and with a minimum of likelihood of destroying the sterility of the hood.

The principal elements of the second form of device include a support member 112 illustrated in FIG. 13 and the hood 120 shown in FIG. 7.

The support member 112 is quite similar to that of the first form, having an adjustable head band 124 to fit around the head of the wearer and also has an adjustable cross band 128 to extend laterally across the head. Mounted on the support member 112 are mask means in the form of a frame 114 that is rigidly connected to the support member, as by rivets, the frame 114 having a certain similarity to the face plate 14 of the first form. However, the frame 114 has a large opening 115 in the central area which corresponds to the major portion of the transparent main body 16 of the first form. The frame does include a portion 162 that corresponds to the margin 62 of the face plate 14 and a portion 160 that is generally spherically curved and has a shape roughly approximating that of a spherical zone. A pair of ventilation conduits 116 are connected to the lower forward end portion of the margin area 162 and extend backward along both sides of the wearer's head to connect to exhaust conduit means (not shown) similar to the exhaust conduit means 18 shown in FIG. 2. The ends of the conduits 116 preferably stop at a point slightly outward from the sides of the chin and are located generally above the lower edge of the chin and below the nostrils. In this way, the person wearing the exhaust mask may freely talk.

The hood 120 is preferably made of a suitable paper or non-woven fabric, and includes a flat, generally elliptical crown 180 and a generally frusto-conical skirt section 182. A face plate 184 is mounted in an opening 185 in the front of the skirt 182 to provide the general appearance shown in FIG. 7.

The face plate 184 has a generally spherical shape and is made of an uncolored transparent plastic, the edges of the plate being turned slightly outwardly to provide flanges 186 to which the edges of the opening 185 in the skirt 182 are cemented. The edges of the opening 115 in the frame 114 are provided with a soft resilient bead 188 so that the face plate 184 will make a sealing fit with the frame 114. The fit of the face plate 184 to the frame 114 is indicated in FIG. 15.

One of the advantages of this second form is found in the convenience in sterilizing the mask and the ease with which it may be applied. Part of this ease of application is provided by the method of folding the hood, and this procedure is illustrated in FIGS. 7 – 12.

A completed hood 120 in its using condition is illustrated in FIG. 7, and to fold the hood for sterilization, the rear of the skirt 182 is folded up and over the crown 180, as indicated by the curved arrow 1 of FIG. 7, thus turning the hood inside out so that it appears as indicated in FIG. 8. In this condition, the hood represents a relatively flat member and the folding may thereafter be conducted upon a table or other suitable working surface.

After the back has been folded over the face plate 184, as previously described, the front lower portion of the skirt 182 is folded up over the face plate, but underneath the back of the skirt, as indicated by the curved arrow 2 in FIG. 7, to provide the relative positions indicated in FIG. 9. At this point, the folded and relatively flat hood 120 has the general appearance indicated in FIG. 10. The skirt 182 projects principally from the sides of the face plate 184 to provide a left arm and a right arm, while the crown 180 projects from the upper edge of the face plate. One of the arms is then folded over the face plate and the other arm then folded over the first arm as indicated in FIG. 11, and finally, the crown 180 is folded over both arms. The resulting package is indicated in FIG. 12.

In this position, the hood 120 can be placed in a suitable container, such as a properly constructed plastic bag (not shown) suitable for gas sterilization, and in this way, the hood may be sterilized while within the plastic bag so that sterility of the hood is maintained during subsequent handling of the plastic bag.

When the hood is to be used, the plastic bag is opened, being careful not to touch the hood with the same means, such as fingers, used to open the plastic bag.

The surgeon or assistant who is to wear the hood 120 will normally have sterile surgical gloves on at this point, and he may then lift the folded hood 120 from the plastic bag and unfold the crown 180 and the two side legs, and then pull down the front of the skirt 182. In each of these actions, he is touching what is to be the interior of the hood 120, so that there is no contamination of the exterior of the hood. He then places the face plate 184 against the frame 114 with the face plate bearing against the sealing member 188 and folds the portion of the skirt 182 still remaining in front of the face plate 184, up and over the top of his head, so that the crown 180 rests upon the top of his head and upon the cross band 128, while the skirt 182 extends down on all sides of him. A surgical gown is then placed on him, with the exhaust conduit projecting from the gown and being attached to suitable exhaust means.

In this condition, the wearer is thus completely covered down to his shoes with sterile covering through which contamination material from the person cannot drop onto the patient. The exhaust system removes the exhalations from the person wearing the protective covering, and the field of vision is substantially the same as that of a person not wearing the hood 120.

From the foregoing, it will be seen that there have been provided two forms of an improved surgical exhaust mask fully capable of securing the advantages and achieving the results heretofore set forth. It is to be understood that modifications may be made in the construction and the patent is not to be limited to the particular form or arrangement of parts herein described and shown, except as restricted by the claims.

I claim:

1. A surgical exhaust mask comprising
a support member sized and shaped to fit on the head of the wearer and including a head band adapted to surround the head in a generally horizontal position;
a removable transparent face plate releasably carried by said support member to extend downwardly from said member and having a spherical configuration;
a suction ventilation conduit opening into the space enclosed by said transparent face plate at the bottom thereof, said conduit at least in part being a flexible tube extending rearwardly and downwardly from said face plate and having its forward portion supported from said support member;
aperture means in the upper portion of the face plate to permit ingress of air from the exterior of said plate and angled inwardly and downwardly to direct the inflow close to the inner surface of the face plate to prevent fogging; and
a hood of flexible sheet material extending over said support member to a point below said face plate and ventilation conduit adapted to enclose the head and shoulders of the wearer, said hood having an opening through which said face plate projects, and the suction from said ventilation conduit drawing said hood against said support member, said face plate, and the head and shoulders of the wearer.

2. A surgical exhaust mask comprising:
a support member sized and shaped to fit on the head of a wearer and including a head band adapted to surround the head in a generally horizontal position;
a removable transparent face plate releasably carried by said support member to extend downwardly from said member and having a spherical configuration, the upper aft portions of the face plate margins being provided with a plurality of vertically spaced connectors cooperating with said support member, to secure the face plate at selected elevations;
a suction ventilation conduit opening into the space enclosed by said transparent face plate at the bottom thereof, said conduit at least in part being a flexible tube extending rearwardly and downwardly from said face plate and having its forward portion supported from said support member and the vertical position of the opening of said conduit being adjustable by means of said vertically spaced connectors; and
a hood of flexible sheet material extending over said support member to a point below said face plate and ventilation conduit adapted to enclose the head and shoulders of the wearer, said hood having an opening through which said face plate projects, and the suction from said ventilation conduit drawing said hood against said support member, said face plate, and the head and shoulders of the wearer.

3. A surgical exhaust mask comprising:
a support member sized and shaped to fit on the head of a wearer and including a head band adapted to surround the head in a generally horizontal position;
mask means comprising a frame member having an outer surface and an inner surface adapted to be adjacent the face of a user, wherein said frame member is attached to said support member and extends from one side to the other and from the head band downwardly, said frame member having a central opening with sealing means on said outer surface of said frame member surrounding said opening at the peripheral edge thereof;

a suction ventilation conduit opening into the space enclosed by said mask means at the bottom thereof, said conduit at least in part being a flexible tube extending rearwardly and downwardly from said mask means;

a hood of flexible sheet material extending over said support member to a point below said mask means to enclose the head and shoulders of the wearer, said hood having an opening aligned with said central opening of said mask means; and a face plate having a peripheral surface complimentally configured to the peripheral edge of said opening in said frame member and attached to said hood and projecting through said opening in said hood, whereby said face plate releasably seals to said frame member when said hood is in place and suction is provided by said conduit.

4. A mask as defined in claim 3, in which said face plate has a lateral spherical configuration of approximately 180° and a vertical spherical configuration of approximately 90°.

5. A surgical exhaust mask comprising:

a support member sized and shaped to fit on the head of a wearer and including a head band adapted to surround the head in a generally horizontal position;

a removable transparent face plate extending downwardly from said support member and having a spherical configuration, the lateral spherical extent being approximately 180° and the vertical spherical extent being approximately 90°, said face plate having apertures in the upper portion thereof to permit ingress of air and angled to direct the inflow close to the inner surface of the face plate to prevent fogging;

a suction ventilation conduit opening into the space enclosed by said transparent face plate at the bottom thereof, said conduit at least in part being a flexible tube extending rearwardly and downwardly from said face plate and having its forward portion supported from said support member; and a hood of flexible sheet material extending over said support member to a point below said face plate and ventilation conduit, adapted to enclose the head and shoulders of the wearer, said hood having an opening through which said face plate projects, the suction from said ventilation conduit drawing said hood against said support member and the head and shoulders of the wearer.

* * * * *